(12) United States Patent
Laine

(10) Patent No.: US 10,435,344 B2
(45) Date of Patent: Oct. 8, 2019

(54) REACTION SEQUENCE FOR THE SYNTHESIS OF NOOTKATONE, DIHYDRONOOTKATONE, AND TETRAHYDRONOOTKATONE

(71) Applicant: Roger Laine, Baton Rouge, LA (US)

(72) Inventor: Roger Laine, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/781,914

(22) PCT Filed: Dec. 8, 2016

(86) PCT No.: PCT/US2016/065598
§ 371 (c)(1),
(2) Date: Jun. 6, 2018

(87) PCT Pub. No.: WO2017/100437
PCT Pub. Date: Jun. 15, 2017

(65) Prior Publication Data
US 2018/0362431 A1    Dec. 20, 2018

Related U.S. Application Data

(60) Provisional application No. 62/265,723, filed on Dec. 10, 2015.

(51) Int. Cl.
| | | |
|---|---|---|
| C07C 45/40 | (2006.01) | |
| C07C 45/68 | (2006.01) | |
| A61K 31/122 | (2006.01) | |
| C07C 29/40 | (2006.01) | |
| C07C 45/51 | (2006.01) | |
| C07C 45/66 | (2006.01) | |
| C07C 45/74 | (2006.01) | |

(52) U.S. Cl.
CPC ............ *C07C 45/40* (2013.01); *A61K 31/122* (2013.01); *C07C 29/40* (2013.01); *C07C 45/512* (2013.01); *C07C 45/66* (2013.01); *C07C 45/68* (2013.01); *C07C 45/74* (2013.01); *C07C 2602/28* (2017.05); *C07C 2602/42* (2017.05)

(58) Field of Classification Search
CPC ...... C07C 45/40; C07C 45/68; C07C 2602/42
See application file for complete search history.

(56) References Cited

U.S. PATENT DOCUMENTS

| | | | | |
|---|---|---|---|---|
| 6,545,186 B2 * | 4/2003 | Giselbrecht | ............ | C07C 45/40 |
| | | | | 568/361 |
| 7,112,700 B1 * | 9/2006 | Sauer | ...................... | C07C 45/28 |
| | | | | 568/348 |

FOREIGN PATENT DOCUMENTS

| | | | | |
|---|---|---|---|---|
| JP | 2008-538363 A | 10/2008 | | |
| WO | WO-2010011134 A2 * | 1/2010 | ............ | C07C 45/40 |
| WO | 2011033047 A1 | 3/2011 | | |

* cited by examiner

*Primary Examiner* — Sikarl A Witherspoon
(74) *Attorney, Agent, or Firm* — Venable LLP; Keith G. Haddaway

(57) ABSTRACT

An inexpensive, stereoselective synthesis for nootkatone, tetrahydronootkatone, and their derivatives is disclosed utilizing ozonolysis. The starting materials used in the synthesis are inexpensive and the reactions are commercially feasible and amenable to scaling up. The principal starting material, (−)-β-Pinene, is on the GRAS list (generally recognized as safe).

18 Claims, No Drawings

REACTION SEQUENCE FOR THE SYNTHESIS OF NOOTKATONE, DIHYDRONOOTKATONE, AND TETRAHYDRONOOTKATONE

PRIORITY

This application claims priority to U.S. Provisional Application No. 62/265,723, filed Dec. 10, 2015, the contents of which are hereby incorporated by reference in the entirety.

FIELD OF THE INVENTION

This invention pertains to the synthesis of nootkatone and its derivatives using ozonolysis.

DESCRIPTION OF THE INVENTION

Nootkatone, with the structure:

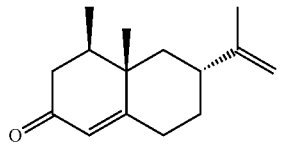 [SMILES: C=C(C)[C@@H]1CCC2=CC(=O)C[C@@H](C)[C@]2(C)C1]

(Compound 9 in Scheme I) occurs naturally in certain plant sources including cedar, vetiver grass, and citrus oils. Nootkatone has a fragrance reminiscent of grapefruit, and is used commercially as a flavor or fragrance ingredient. Nootkatone is nontoxic to humans and other mammals, regarded as a GRAS substance by FDA.

Nootkatone also has activity as a repellant or toxicant against various arthropods, including termites, ants, flies, mosquitos, fleas, lice, ticks, mole crickets, and cockroaches; as well as against certain other invertebrates including nematodes. No new commercially viable insect repellents have been marketed since DEET, the major component in current insect repellants. The spread of diseases like Lyme's disease by ticks, dengue, chikengunya, Zika and malaria by mosquitos drives a need for more products to repel these insects. Nootkatone also acts as an environmentally-friendly wood and art preservative. See, e.g., International Patent Application Publication No. WO 01/28343; and U.S. Pat. No. 6,906,108; each of which is incorporated herein by reference in its entirety.

The excessive cost of commercially preparing nootkatone impedes its broader use for these and other purposes outside flavors and fragrances. Although nootkatone has been known and used for some time, a means of commercially preparing the compound and its derivatives, particularly through synthetic methods, has been elusive. Thus, there is a long felt unfilled need for an efficient and economical synthesis of nootkatone, tetrahydronootkatone, and other nootkatone derivatives. A successful synthesis is preferably stereoselective, so that the products have the desired biological activity; and based on starting materials that are on the GRAS (generally recognized as safe) list, to reduce the burdens of regulatory approval. Most of the nootkatone sold commercially to date has been produced by the semisynthetic oxidation of the orange oil component valencene. Valencene is an expensive starting material, but a viable commercial production that avoids its use has yet to be developed.

Prior synthetic methods for preparing nootkatone have one or more of the following disadvantages: the synthesis is lengthy; the synthesis requires relatively expensive starting materials; the yield is low; purification of intermediates is required; use of excessive solvents creates waste problems for commercial production; difficult to dispose of by-products; the synthesis produces a racemic mixture; or one or more starting materials are not on the GRAS list.

Accordingly, there is an unfilled need for a less expensive method for the stereoselective synthesis of nootkatone. While the current high price of nootkatone may be tolerable in certain fields of use, such as flavorings and fragrances, the absence of a less expensive source of nootkatone precludes commercial use in other areas, for example as a repellant or toxicant against termites, ticks, mosquitos or other pests. If nootkatone could be produced far more inexpensively than is currently the case, it would become commercially feasible to use it and its derivatives as a repellant or toxicant against various arthropods, including termites, ants, flies, ticks, mole crickets, fleas, lice and cockroaches; as well as against certain other invertebrates such as nematodes. It could also become commercially feasible to use it as a wood and artwork preservative for protection against wood-destroying insects. U.S. Pat. No. 7,112,700, incorporated herein by reference in its entirety, provides an efficient and economic asymmetric synthesis of nootkatone and has reduced the length synthetic steps of making nootkatone and derivatives. However, an improved process is desirable for large scale industrial production of nootkatone that requires fewer purification steps, lower solvent requirements, with less byproducts, and that produces higher yields. Therefore, improvements are necessary to further modify the synthetic pathway to facilitate viable commercial production of nootkatone. Such syntheses could provide a lower cost of production and utilize commercially feasible and scalable reactions.

The present invention provides a novel, inexpensive, stereoselective synthesis for nootkatone, dihydronootkatone, tetrahydronootkatone, and their derivatives utilizing ozonolysis in particular steps. An exemplary synthesis of nootkatone is provided in Scheme I.

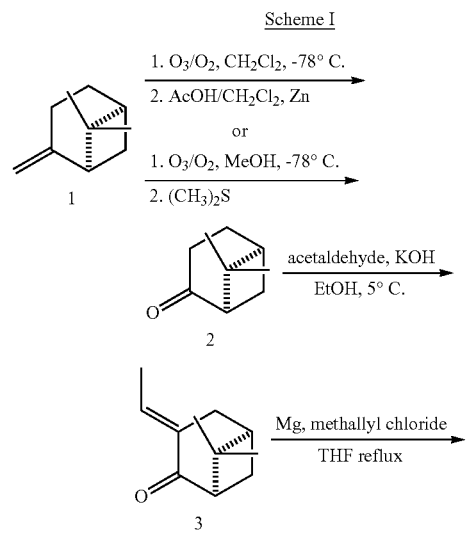

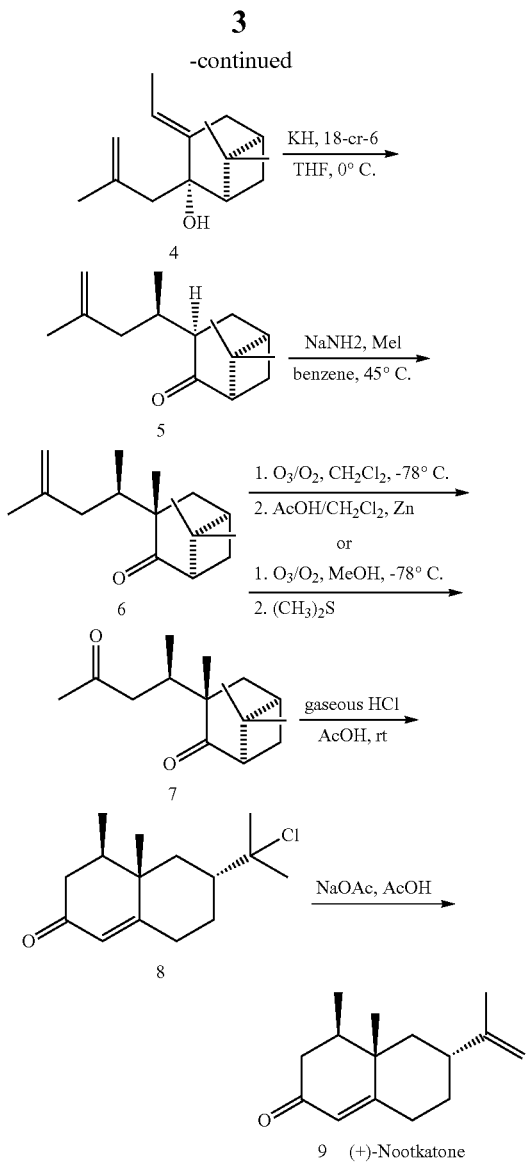

The starting materials used in the synthesis are inexpensive. The principal starting material, (−)-β-Pinene, is a natural compound on the GRAS list. The synthesis is shorter, less expensive, more efficient and of significantly higher yield than prior synthetic schemes for nootkatone. The process of making nootkatone is improved by, for example, avoiding the use of alumina, the need to purify intermediate products using column chromatography, and limited use of solvents. In particular, the present invention improves upon prior synthesis by utilizing ozonolysis to convert (−)-β-pinene to produce nopinone in good yield and without further purification before continuing the synthesis. The invention also utilizes ozonolysis to convert 3-(1,3-dimethyl-but-3-enyl)-3,6,6-trimethyl-bicyclo[3.1.1]heptan-2-one (Compound 6) to (1R, 3S, 5R)-3-[(1R)-1-Methyl-3-oxobutyl]-3,6,6-trimethylbicyclo[3.1.1]heptan-2-one (Compound 7), also without need of purification to conduct the next synthetic steps.

Experimental data show that the synthetic scheme outlined in Scheme I stereoselectively yields nootkatone as the exclusive product. The starting material was converted to this single product.

Nootkatone made through this synthesis may also be used as an intermediate in preparing nootkatone derivatives, some of which also have activity in repelling termites and other invertebrate pests. For example, following the methods of K. Stevens et al., "Odour character and threshold values of nootkatone and related compounds," *J. Sci. Fd. Agric.*, vol. 21, pp. 590-593 (1970), nootkatone may be converted into isonootkatone, tetrahydronootkatone, 11,12-dihydronootkatone, or 1,10-dihydronootkatone. Following the methods of B. Zhu et al., "Structure-activity of valencoid derivatives and their repellence to the Formosan subterranean termite," *J. Chem. Ecol.*, vol. 29, pp. 2695-2701 (2003), nootkatone may be converted into nootkatol. Following the methods of U.S. Pat. No. 7,112,700, nootkatone may be converted into isonootkatone, dihydronootkatone, or tetrahydronootkatone.

The invention is further exemplified by the following non-limiting examples.

Example 1A 6,6-Dimethyl-bicyclo [3.3.1]heptan-2-one, Nopinone (Compound 2)

A solution of β-Pinene (Compound 1) (40.0 g, 294 mmol) in 160 ml $CH_2Cl_2$ was chilled on dry ice at −78° C., and ozone/$O_2$ bubbled through overnight until a blue color persisted. Nitrogen was then bubbled through the reaction mixture for 30 minutes. $CH_2Cl_2$ (160 ml) was added followed by AcOH (80 ml). At 0° C., Zn (40 g) was added in 1 g portions over 4 hours, dry ice was added to the solution to control temperature. The solution was spun on a rotavap at 30° C. for 1 hour. TLC (10% EtOAc/Hexane, 5% $H_2SO_4$/EtOH stain) showed the reaction was complete. Then 300 ml water was added and stirred for 10 minutes. Zn was removed by filtration and rinsed with $CH_2Cl_2$. The $CH_2Cl_2$ layer was separated and washed with water again, then washed with saturated $Na_2CO_3$ solution, followed by brine, dried over $MgSO_4$, and concentrated, 33.1 g (82% yield) colorless oil was obtained. The crude product was used directly for the next step. $^1$H NMR: (250 MHz, $CDCl_3$), δ 2.7-2.5 (m, 3H), 2.42-2.29 (m, 1H), 2.27-2.2 (m, 1H), 2.13-1.87 (m, 2H), 1.61-1.57 (d, J=9.46, 1H), 1.33 (s, 3H), 0.86 (s, 3H). $^{13}$C NMR: (62.5 MHz, $CDCl_3$), δ 214.77, 57.94, 41.10, 40.30, 32.57, 25.88, 25.17, 22.10, 21.31.

Example 1B 6,6-Dimethyl-bicyclo [3.3.1]heptan-2-one, Nopinone (Compound 2)

Ozone was bubbled through a solution of β-Pinene (Compound 1) 4.60 mL (29.36 mmol, 1 equiv) in MeOH (7 mL) at −78° C. After 3 hours, 02 was bubbled through for an additional 30 minutes after which the characteristic blue color in the solution indicated excess ozone and consumption of the substrate. After addition of $(CH_3)_2S$ (3.7 mL, 49.91 mmol, 1.7 equiv) the mixture was allowed to warm to room temperature and stirred for an additional 12 hours. The reaction mixture was transferred to a separatory funnel and diluted with $CH_2Cl_2$ (10 mL) and $H_2O$ (10 mL). The organic phase was collected and aqueous layer extracted with $CH_2Cl_2$ (2×10 mL). The combined organic extracts were washed with brine and dried using $Na_2SO_4$. Concentration under reduced pressure afforded an oil. Flash column chromatography on silica gel using 3.5% to 8.5% EtOAc in hexanes as the eluent afforded the title compound as a clear oil confirmed by NMR spectroscopy. 3.812 g, 93% yield.

Example 2

(1R,5R)-6,6-Dimethyl-3-E-ethylidenebicyclo[3.3.1]heptan-2-one (Compound 3)

A solution of Nopinone (9.9 g, 71.6 mmol) and EtOH (172 ml) was cooled to 5° C., while stirring KOH (4.72 g) was added. Acetaldehyde (5.74 ml in 43 ml EtOH) was added to the reaction during 30 minutes. Four additional portions of acetaldehyde (same amount) were added to the solution at intervals of 12 h. The reaction was stirred for another 6 hours. Para-toluenesulfonic acid monohydrate was added, and then the solution was concentrated on a rotavap. A small amount of $CH_2Cl_2$ was added to dissolve the residue, and then hexane was added and the solution swirled. The solution was transferred to another flask and concentrated. After flash chromatography (10% EtOAc in Hexane), a colorless oil (8.6 g, 73% yield) was obtained. It was further purified with Kugelrohr distillation (250° C., 10 mmHg) to give 6.5 g product (55% yield). $^1H$ NMR: (250 MHz, $CDCl_3$), δ 6.89-6.86 (m, 1H), 2.59-2.56 (m, 4H), 2.21 (m, 1H), 1.81-1.77 (m, 3H), 1.46 (m, 1H), 1.35 (s, 3H), 0.86 (s, 3H). $^{13}C$ NMR: (62.5 MHz, $CDCl_3$), δ 202.48, 134.76, 134.00, 55.5, 40.5, 38.98, 27.9, 27.8, 26.2, 21.6, 13.7.

As an alternative, NaOH may be used as the base in this synthesis, in lieu of KOH.

Example 3

3-Ethylidene-6,6-dimethyl-2-(2-methyl-allyl)-bicyclo[3.1.1]heptan-2-ol (Compound 4)

Mg (2.04 g, 84 mmol) was placed in a round bottom flask with THF (27 ml). The solution was stirred while refluxing. Methallyl chloride (5.4 ml, 54 mmol) was mixed with THF (9 ml) and added slowly to the Mg/THF suspension. After addition of the first 2 ml, the heater was removed when the heat released in the reaction maintained refluxing of the solution during addition of the methallyl chloride. When the addition was complete, the heater was put back and the reaction refluxed for additional 30 minutes. The solution was cooled to −78° C. Compound 3 (2.94 g, 18 mmol) was mixed with THF (9 ml), and added to the Grignard solution dropwise over 2 minutes. When TLC showed the reaction was complete (5% EtOAc in Hexane, product spot above the starting material spot), the reaction was diluted with 45 ml THF, and $H_2O$ added (2 ml) dropwise. After swirling, the solution became clear. The solution was transferred to another flask, concentrated and subjected to flash chromatography (5% EtOAc in Hexane). The product 3.43 g (87% yield) was isolated as a colorless oil. $^1H$ NMR: (250 MHz, $CDCl_3$), δ 0.973 (s 3H), 1.05-1.01 (d 1H), 1.21 (s 3H), 1.60-1.57 (d oft, 3H), 1.61 (s 3H), 1.92 (s 3H), 2.63-2.18 (m 5H), 4.82-4.65 (m 2H), 5.79-5.77 (m 1H); $^{13}C$ NMR (62.5 MHz, $CDCl_3$) δ 13.1, 22.4, 24.7, 27.3, 30.1, 31.6, 37.9, 38.7, 48.9, 49.8, 78.7, 114.4, 122.0, 143.2, 143.4.

Example 4

General Procedure for Oxy-Cope Rearrangement (Conversion of Compound 4 to Compound 5):

Under an argon atmosphere, oil-free potassium hydride, KH, (4.1 mmol) was placed in a round bottom flask. Freshly distilled THF (35 mL) was cannulated into the flask, and the contents were stirred at 0° C. Compound 4 (2.4 mmol) was added to the flask, followed immediately by a solution of 18-crown-6 in THF (2.4 mmol) via cannulation. The mixture was allowed to react at 0° C. for about 6 hours. The reaction was then quenched with a phosphate buffer solution (pH=7), and the contents were extracted with ether. The combined organic layers were washed with water and brine, and dried over $Na_2SO_4$. After filtration, excess solvent was removed under vacuum to provide crude 3-(1,3-dimethyl-but-3-enyl)-6,6-dimethyl-bicyclo[3.1.1]heptan-2-one (Compound 5). Purified Compound 5 (0.49 g, 71%) was obtained by column chromatography (with a 90:10/Hexane: EtOAc solvent). $^1H$ NMR: (250 MHz, $CDCl_3$), δ 0.79 (s 3H), 0.93-0.90 (d 3H), 1.32 (s 3H), 1.73-1.68 (s and q overlapping, 5H), 2.12-1.95 (m 3H), 2.42-2.25 (m 1H), 2.47-2.43 (in 1H), 2.57-2.50 (in 2H), 2.65-2.60 (m, —OH, 1H), 4.764.71 (d 2H); $^{13}C$ NMR (62.5 MHz, $CDCl_3$) δ 15.3, 21.2, 21.8, 25.8, 26.8, 27.6, 40.6, 43.2, 43.5, 44.9, 57.9, 111.9, 144.0, 215.9.

Alternative phase transfer agents or metal-chelating agents might be used in lieu of 18-crown-6 in the Oxy-Cope reaction to reduce costs, for example quaternary ammonium compounds (quats), PEG [poly(ethyleneglycol)], or tris[2-(2-methoxyethoxy)ethyl]amine.

Example 5

General Procedure for Methylation (Conversion of Compound 5 to Compound 6):

Sodium amide (3.64 mmol, assay 90%) was placed in a round bottom flask fitted with a reflux condenser, evacuated, and then purged with nitrogen. Freshly distilled benzene (dried over Na/benzophenone) was cannulated into the apparatus, and the mixture was warmed with a heating mantle. The ketone Compound 5 (1.2 mmol) was then injected, and the reaction mixture was refluxed with continual stirring for 5 hours. The reaction was then cooled to 45° C. (via a hot water bath), and iodomethane (2.9 mmol) (freshly distilled and dried over Drierite) was injected as a single portion. An additional portion of iodomethane (1.57 eq.) was injected 2.5 hours later, and the solution was allowed to react at 45° C. for an additional 15 hours. Saturated aqueous $NH_4Cl$ was then added to the cooled solution, and the product was extracted with ethyl ether. The organic layer was then washed with water and brine, and dried over $Na_2SO_4$. Removal of excess solvent under vacuum provided crude product 6.

As an alternative, toluene may be used as solvent in this synthesis, in lieu of benzene.

3-(1,3-dimethyl-but-3-enyl)-3,6,6-trimethyl-bicyclo[3.1.1]heptan-2-one (Compound 6): Purified Compound 6 (0.25 g, 78%) was obtained by column chromatography (with a 90:10/Hexane: EtOAc solvent). $^1H$ NMR: (250 MHz, $CDCl_3$), δ 0.89-0.87 (s and d overlapping, 6H), 1.31 (s 3H), 1.33 (s 3H), 1.70 (s 3H), 1.80-1.73 (m 2H), 2.13-1.89 (m 3H), 2.30-2.22 (q 1H), 2.49-2.36 (m 1H), 2.60-2.56 (t 1H), 3.12-3.01 (brd, 1H), 4.72-4.67 (d 2H); $^{13}C$ NMR (62.5 MHz, $CDCl_3$) δ 14.7, 21.8, 22.3, 25.8, 26.6, 35.2, 38.1, 40.7, 41.7, 43.1, 45.9, 59.5, 111.3, 145.1, 219.2.

Example 6

(1R, 3S, 5R)-3-[(1R)-1-Methyl-3-oxobutyl]-3,6,6-trimethylbicyclo[3.1.1]heptan-2-one (Compound 7)

Starting from Compound 6: A solution of Compound 6 (0.25 g, 1.1 mmol) in 2 ml $CH_2Cl_2$ was chilled on dry ice at −78° C., and bubbled with ozone/$O_2$ for overnight until a blue color persisted. Nitrogen was then bubbled through the reaction mixture for 30 minutes. Then 2 ml $CH_2Cl_2$ was added followed by 1 ml AcOH. At 0° C., 0.5 g zinc was added in 100 mg portions over 4 hours. Then the solution was spun on rotavap at 30° C. for 1 hour. TLC (15% EtOAc/Hexane, and 5% H₂SO₄/EtOH TLC stain) showed the reaction was complete. Then 3 ml water was added and stirred for 10 minutes. Zn was removed by filtration and rinsed by CH₂Cl₂. The CH₂Cl₂ layer was separated and washed with water again, then washed with saturated Na₂CO₃ solution, followed by brine. Dried over MgSO₄, and then was concentrated, 0.2 g (90% yield) colorless oil was obtained and identified as Compound 7. The crude product was used directly for the next step without need of purification. $^1$H NMR: (250 MHz, CDCl₃), δ 0.85-0.82 (d and s overlapping, 6H), 1.17 (s 3H), 1.24 (s 3H), 1.78-1.72 (m 2H), 1.93-1.85 (2 br s, 1H), 2.09-1.96 (in 1H), 2.09 (s 3H), 2.24-2.12 (m 1H), 2.42-2.27 (m 1H), 2.58-2.47 (in 2H), 3.58-3.52 (in 1H); $^{13}$C NMR (62.5 MHz, CDCl₃) δ 16.4, 22.6, 24.8, 25.7, 26.3, 30.4, 35.1, 36.9, 41.6, 42.7, 44.6, 47.3, 59.5, 208.2, 219.9.

Alternatively, after ozonolysis is complete, (CH₃)₂S can be added followed by allowing the mixture to warm to room temperature and stirring until the reaction is complete. The reaction mixture is diluted with CH₂Cl₂ and H₂O, the organic phase collected and the aqueous layer extracted with CH₂Cl₂. The combined organic extracts are washed with brine, dried using Na₂SO₄ and concentrated. The product can be further purified, if necessary.

Example 7

(4R,4aS,6R)-4,4a,5,6,7,8-Hexahydro-4,4a-dimethyl-6-(1-chloro-1-methylethyl)-2(3H)-naphthalenone (Compound 8)

A dry 3-neck round bottom flask was fitted with a porous gas frit and two gas flow adapters. Under a steady stream of argon, the flask was charged with a solution of purified Compound 7 in glacial acetic acid (99.6%, Aldrich). Anhydrous, gaseous HCl (lecture bottle, Aldrich) was bubbled through the porous fit at room temperature until the solution was saturated with HCl. After 21 hours stirring at room temperature, the mixture was poured into ice, and was then extracted with dichloromethane. The organic layer was washed with water, washed with brine, dried over MgSO₄, filtered, and concentrated via the rotary evaporator to provide the crude material in oil form. Recrystallization from hexane provided Compound 8 as colorless needles. Yield, 74%. $^1$H NMR: (250 MHz, CDCl₃), δ 5.75 (s, 1H), 2.53-2.34 (m, 2H), 2.31-2.22 (m, 2H), 2.20-1.91 (m, 4H), 1.59 (d, 6H, CH₃, J=4.3 Hz), 1.39-1.25 (m, 2H), 1.10 (s, 3H, CH₃), 1.00-0.97 (d, 3H, CH₃, J=6.76 Hz); $^{13}$C NMR (62.5 MHz, CDCl₃) δ 199.7, 170.1, 124.9, 74.1, 45.8, 42.4, 40.8, 40.5, 39.5, 32.3, 30.9, 30.5, 28.5, 17.3, 15.3.

Example 8

Nootkatone (Compound 9):

Sodium acetate trihydrate (0.22 g, 1.6 mmol) was added to a single-neck round bottom flask fitted with a reflux condenser. A solution of the chloroenone Compound 8 (0.14 g, 0.54 mmol) in glacial acetic acid (4 mL) was injected into the flask, and the mixture was heated to 100° C. and held at that temperature for 2 hours. The reaction mixture was then cooled to room temperature, poured into cold water, and extracted with chloroform. The organic layer was then washed with successive portions of 2% aqueous KOH, 2 N HCl, NaHCO₃, and brine, and then dried over MgSO₄. The excess solvent was removed via rotary evaporator to provide nootkatone as a yellow oil (93%). Because the Oxy-Cope reaction and the methylation both provided the desired enantiomeric product, the enantiomeric purity of the final nootkatone product was not changed from that of the β-pinene starting product. Qualitatively, the fragrance of the synthesized nootkatone was identical to the fragrance of nootkatone derived from other sources. NMR data matched that previously reported for nootkatone: $^1$H NMR: (250 MHz, CDCl₃), δ 5.77 (s, 1H), 4.75-4.72 (m, 2H), 2.62-2.43 (m, 1H), 2.41-2.22 (m, 4H), 2.09-1.87 (M, 3H), 1.46-1.38 (m, 1H), 1.12-1.10 (m, 4H), 0.98 (d, 3H).

The complete disclosures of all references cited in this specification are hereby incorporated by reference. In the event of an otherwise irreconcilable conflict, however, the present specification shall control.

What is claimed is:

1. A method of synthesizing nootkatone comprising the steps of:
   ozonolysis of Compound 6

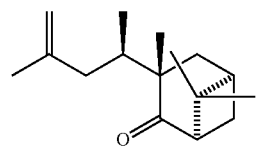

to produce crude Compound 7

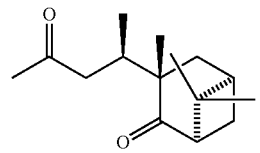

without purification;
   converting crude Compound 7 to produce Compound 8

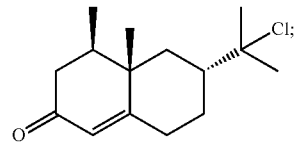

and
   converting compound 8 to nootkatone.

2. The process of claim 1, wherein the ozonolysis step comprises
   oxidizing Compound 6 with ozone/O₂ in MeOH; and
   adding (CH₃)₂S to produce Compound 7.

3. The process of claim 1, wherein the ozonolysis step comprises
   oxidizing Compound 6 with ozone/O₂ in CH₂Cl₂; and
   adding AcOH and zinc to produce Compound 7.

4. The process of claim 1, further comprising the steps of:
   ozonolysis of β-pinene (Compound 1)

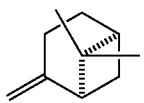

to produce crude nopinone (Compound 2)

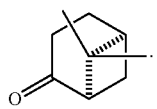

without purification; and
converting crude nopinone to Compound 6

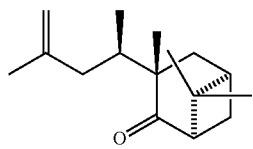

through intermediate steps.

5. The process of claim 4, wherein the ozonolysis of β-pinene comprises
oxidizing β-pinene with ozone/$O_2$ in MeOH; and
adding $(CH_3)_2S$ to produce Compound 2.

6. The process of claim 4, wherein the ozonolysis of β-pinene comprises
oxidizing β-pinene with ozone/$O_2$ in $CH_2Cl_2$; and
adding AcOH and zinc to produce Compound 2.

7. A process of making a nootkatone derivative comprising the steps of:
ozonolysis of Compound 6

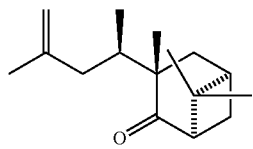

to produce crude Compound 7

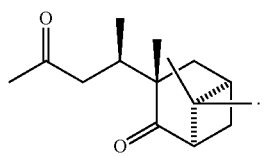

without purification;
converting crude Compound 7 to produce Compound 8

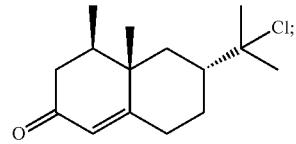

and
converting compound 8 to nootkatone.

8. The process of claim 7, wherein the ozonolysis step comprises
oxidizing Compound 6 with ozone/$O_2$ in MeOH; and
adding $(CH_3)_2S$ to produce Compound 7.

9. The process of claim 7, wherein the ozonolysis step comprises
oxidizing Compound 6 with ozone/$O_2$ in $CH_2Cl_2$; and
adding AcOH and zinc to produce Compound 7.

10. The process of claim 7, further comprising the steps of:
ozonolysis of β-pinene (Compound 1)

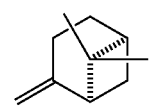

to produce crude nopinone (Compound 2)

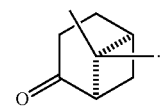

without purification; and
converting crude nopinone to Compound 6

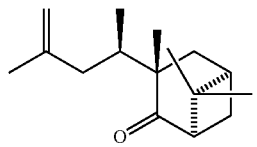

through intermediate steps.

11. The process of claim 10, wherein the ozonolysis step comprises
oxidizing β-pinene with ozone/$O_2$ in MeOH; and
adding $(CH_3)_2S$ to produce Compound 2.

12. The process of claim 1, wherein the ozonolysis of Compound 6 comprises
oxidizing β-pinene with ozone/$O_2$ in $CH_2Cl_2$; and
adding AcOH and zinc to produce Compound 2.

13. The process of claim 7, wherein the nootkatone derivative is selected from the group consisting of isonootkatone, tetrahydronootkatone, 11,12-dihydronootkatone, 1,10-dihydronootkatone, nootkatol, and dihydronootkatone.

14. The process of claim 13, wherein the nootkatone derivative is selected from the group consisting of isonootkatone, dihydronootkatone, and tetrahydronootkatone.

15. The process of claim 4, wherein converting crude nopinone to Compound 6 comprises the steps of:

converting the crude nopinone to

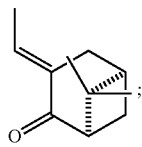

converting

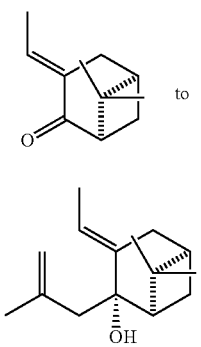

to converting

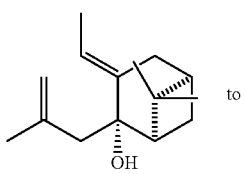

to

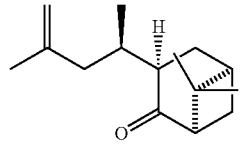

to Compound 6.

16. The process of claim 15, wherein the crude nopinone is reacted with acetaldehyde and a base to produce

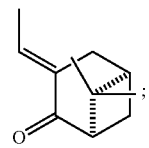

wherein

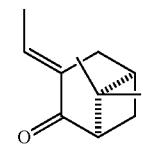

is reacted with methallyl chloride and a metal to produce

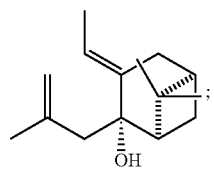

wherein

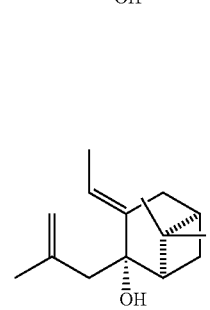

is subjected to Oxy-Cope rearrangement to produce

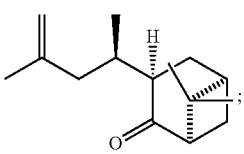

wherein

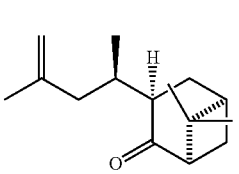

is reacted with a methyl halide and a base to produce Compound 6.

17. The process of claim 7, wherein converting crude nopinone to Compound 6 comprises the steps of:

converting the crude nopinone to

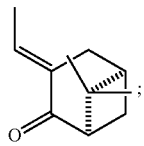

converting

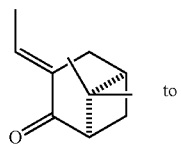 to

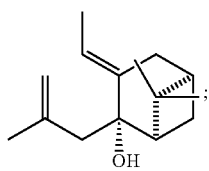

converting

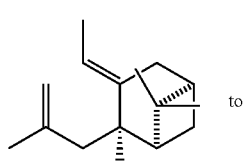 to

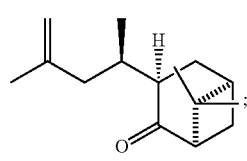

converting

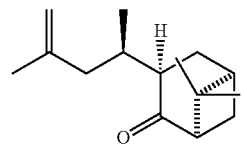

to Compound 6.

18. The process of claim 17, wherein the crude nopinone is reacted with acetaldehyde and a base to produce

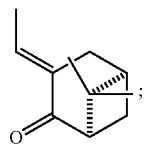

wherein

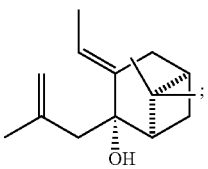

is reacted with methallyl chloride and a metal to produce

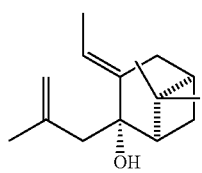

wherein

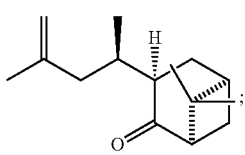

is subjected to Oxy-Cope rearrangement to produce

5 wherein

5 is reacted with a methyl halide and a base to produce Compound 6.

* * * * *